United States Patent [19]

Cervantes et al.

[11] Patent Number: 5,756,076
[45] Date of Patent: May 26, 1998

[54] CONDITIONING COMPOSITION AND DETERGENT FOR USE ON HAIR

[75] Inventors: Frédéric Cervantes; Juan Lopez, both of Paris, France

[73] Assignee: L'Oreal, Paris, France

[21] Appl. No.: 708,616

[22] Filed: Sep. 5, 1996

[30] Foreign Application Priority Data

Sep. 7, 1995 [FR] France .................... 95 10484

[51] Int. Cl.$^6$ .................... A61K 7/06
[52] U.S. Cl. .................... 424/70.1; 424/70.27; 514/880; 514/881
[58] Field of Search .................... 424/70.1, 70.27; 514/880, 881

[56] References Cited

U.S. PATENT DOCUMENTS 4,563,347  1/1986  Starch ........................ 424/70

Primary Examiner—Terressa Mosley
Attorney, Agent, or Firm—Finnegan, Henderson, Farabow, Garrett & Dunner, L.L.P.

[57] ABSTRACT

The present invention relates to a cosmetic conditioning and detergent composition for the hair which is stable and comprises, in an aqueous medium:

(A) a conditioner system comprising at least one $C_{14}$–$C_{22}$ fatty alcohol and at least one cationic surfactant selected from quaternary ammonium salts, and, optionally, at least one cationic silicone, and (B) a washing base comprising at least one alkylpolyglycoside nonionic surfactant, and optionally at least one amphoteric or zwitterionic surfactant, and (C) a stabilizer system comprising at least one stearate selected from glycol monostearates and glycol distearates and at least one crosslinked polymer of methacryloyloxyethyltrimethylammonium chloride.

Also disclosed is a method for the simultaneous care and washing of hair.

25 Claims, No Drawings

CONDITIONING COMPOSITION AND DETERGENT FOR USE ON HAIR

The present invention relates to a cosmetic composition which is both conditioning and detersive for the simultaneous care and washing of the hair. The invention also relates to the use of this composition for the simultaneous care and washing of the hair.

It is known that hair must be cleaned regularly to remove the dirtiness caused by the secretion of sebum and the surrounding atmosphere.

The washing bases which are used for this purpose, and which consist of surfactants with detersive and foaming power, most frequently anionic surfactants, get rid of the dirtiness and sebum from the hair but leave it in a condition in which it is difficult to style. With these traditional shampoos, the hair becomes dry or goes frizzy, lacks sheen and softness to the touch after it has been dried, and is difficult to disentangle in the dried and wetted state. Sometimes, it is charged with static electricity as well. These disadvantages are accentuated all the more when the hair has been subjected to chemical hair treatments (dyeing, bleaching, perming, etc.) or has been attacked by light, or else when the hair is fine.

In order to remedy these disadvantages, a solution has been proposed which consists in carrying out—after shampooing and therefore in a second stage—the application of hair-conditioning agents, which are left to act for some time and then rinsed off under running water (so-called conditioner compositions). Another solution consists in avoiding this second stage, which undesirably prolongs treatment, by including a hair-conditioning agent directly in the shampoo itself (so-called conditioning shampoo compositions).

The conditioning agents present in conventional conditioner compositions are fatty alcohols and cationic surfactants, and impart to the hair a soft feel, ease of disentangling and an antistatic effect. These conditioners, which are intended to improve the cosmetic properties of the hair, do not themselves have any washing property.

As far as the abovementioned conditioning shampoos are concerned, the majority contain, in addition to the usually anionic washing base, cationic conditioning agents. However, one of the problems which may arise with this type of composition is that of the possibility of harmful interaction between the anionic surfactants, which are good detergents, and certain cationic conditioning agents, thereby limiting the effectiveness of the composition.

In order to avoid this problem, conditioning shampoos have been proposed which contain nonionic surfactants such as, for example, alkylpolyglycosides, which have advantageous detergent and foaming properties, in combination with cationic polymers and/or silicones. Such compositions are described in the patent applications EP-0 337 354 and EP-0 398 177. However, these shampoos are still not completely satisfactory and do not condition the hair as well, especially in terms of softness on wetted hair during and after application, as the abovementioned conditioner compositions.

There is therefore still a need for a conditioning composition for the hair which is also able to wash the hair in a single step and to impart conditioning properties which are at least equal, if not superior, to those exhibited by conventional conditioners, and which, moreover, have a satisfactory property of stability.

The present invention aims to meet this need by providing, in a preferred embodiment, conditioning and detergent compositions which are sufficiently foaming and are stable, and which have conditioning properties, especially properties of softness of wetted hair, which are equal or superior to those of the conventional conditioner compositions based on fatty alcohols and cationic surfactants.

Thus, after much research carried out in this matter, the inventors have now discovered, completely unexpectedly and surprisingly, that by combining (A) a conditioner system comprising at least one $C_{14}$–$C_{22}$ fatty alcohol and at least one cationic surfactant selected from quaternary ammonium salts, (B) a washing base comprising at least one alkylpolyglycoside nonionic surfactant, and (C) a stabilizer system comprising at least one stearate selected from glycol monostearates and glycol distearates and at least one crosslinked polymer of methacryloyloxyethyltrimethylammonium chloride, it is possible to obtain a stable, foaming composition which both conditions and washes the hair while providing results which are at least equal to those obtained by a two-stage process requiring, in a first stage, washing with a conventional shampoo and, in a second stage, application of a conditioner comprising a fatty alcohol and a conditioning agent of the cationic surfactant type.

It is this discovery which forms the basis of the present invention.

Therefore, a subject of the present invention is a novel conditioning and detergent composition for hair, which is characterized in that it comprises, in an aqueous medium:

(A) a conditioner system comprising (i) at least one $C_{14}$–$C_{22}$ fatty alcohol and (ii) at least one cationic surfactant selected from quaternary ammonium salts, and optionally (iii) at least one cationic silicone, (B) a washing base comprising (i) at least one alkylpolyglycoside nonionic surfactant, and optionally (ii) at least one amphoteric or zwitterionic surfactant, the amphoteric surfactant being selected more particularly from the betaines, and (C) a stabilizer system comprising (i) at least one stearate selected from glycol monostearates or glycol distearates and (ii) at least one crosslinked polymer of methacryloyloxyethyltrimethylammonium chloride.

A detailed description of the present invention will now be given.

A—CONDITIONER SYSTEM

The at least one $C_{14}$–$C_{22}$ fatty alcohol which can be used is selected, preferably, from cetyl alcohol, stearyl alcohol and cetyl stearyl alcohol. A particularly preferred fatty alcohol according to the invention is 50/50 cetyl stearyl alcohol (% calculated by weight).

The cationic surfactant or surfactants comprise, according to the invention, quaternary ammonium salts, among which it is possible to mention:

those having the following general formula (I):

in which the radicals $R_1$ to $R_4$, which can be identical or different, are an aliphatic radical containing 1 to approximately 22 carbon atoms, or an aromatic, alkoxy, polyoxyalkylene, alkylamide, hydroxyalkyl, aryl or alkylaryl radical containing approximately 12 to approximately 22 carbon atoms or a ($C_{12}$–$C_{22}$)alkylamido($C_2$–$C_6$)alkyl radical or a ($C_{12}$–$C_{22}$)alkoxycarbonyl($C_1$–$C_4$)alkyl radical; $X^-$ is an anion chosen from halides, phosphates, acetates, lactates, alkyl sulphates alkylsulphonates, and alkylarylsulphonates.

quaternary ammonium salts of the imidazolinium type, for example that of the following formula (II):

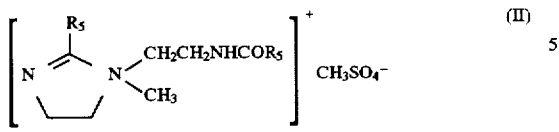

in which $R_5$ is independently selected from alkenyl and alkyl radicals containing 13 to 21 carbon atoms and derivatives of tallow fatty acids, such as the product sold under the tradename "REWOQUAT W 7500" by REWO, the quaternary diammonium salts of formula (III):

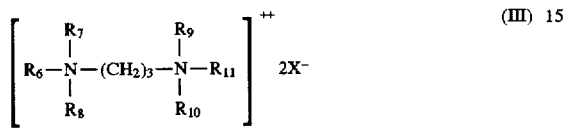

in which $R_6$ is an aliphatic radical containing approximately from 16 to 22 carbon atoms, $R_7$, $R_8$, $R_9$, $R_{10}$ and $R_{11}$ are chosen from hydrogen or an alkyl radical containing from 1 to 4 carbon atoms, and $X^-$ is an anion chosen from halides, acetates, phosphates and sulphates. Such quaternary diammonium salts include, in particular, propane-tallow-diammonium dichloride.

Among the quaternary ammonium salts of formula (I) preference is given, on the one hand, to tetraalkylammonium chlorides, for example, dialkyldimethylammonium chlorides or alkyltrimethylammonium chlorides, in which the alkyl radical contains approximately 12 to approximately 22 carbon atoms, especially behenyltrimethylammonium chloride, distearyldimethylammonium chloride or cetyltrimethylammonium chloride, or else, on the other hand, the stearamidopropyldimethyl(myristyl acetate)ammonium chloride sold under the tradename "CERAPHYL 70" by VAN DYK.

According to the invention, behenyltrimethylammonium chloride is the most particularly preferred quaternary ammonium salt.

According to the invention, the conditioner system may additionally contain, if desired, a cationic silicone.

Such cationic silicones include, in particular, the polymer of formula (IV):

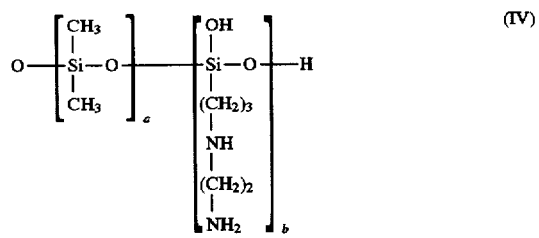

in which a and b are integers depending on the molecular weight, the number average molecular weight being approximately from 5000 to 10,000. This polymer is known under the name "Amodimethicone" in the CTFA dictionary.

A product comprising this type of polymer, and which is more particularly preferred here, is that sold under the tradename "DC 939 cationic emulsion" (or DC 939) by Dow Corning, which is a combination of amodimethicone, hexadecyltrimethylammonium chloride and polyethoxylated tridecyl alcohol, in an aqueous emulsion containing 36% of amodimethicone.

Other cationic silicones which can be used according to the present invention are polymers of formula (V):

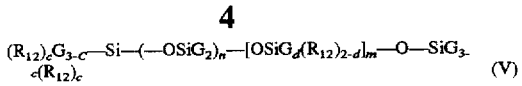

in which

G is selected from H, OH, $C_{1-8}$ alkyl and phenyl, and is preferably methyl, a is 0 or an integer ranging from 1 to 3, and is preferably 0, b is 0 or 1, and is preferably 1, the sum (n+m) represents a number ranging from 0 to 2000, preferably from 50 to 150, n possibly being a number ranging from 0 to 1999, and preferably from 49 to 149, and m possibly being a number ranging from 1 to 2000, preferably from 1 to 10, $R_{12}$ is a monovalent radical of formula $C_qH_{2q}L$ in which q=2 to 8, L being selected from the groups:

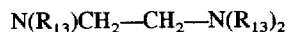
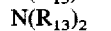
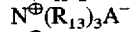

$N(R_{13})CH_2$—$CH_2$—$N(R_{13})_2$
$N(R_{13})_2$
$N^{\oplus}(R_{13})_3 A^-$
$N^{\oplus}(R_{13})CH_2$—$CH_2$—$N^{\oplus}(R_{13})H_2 A^-$ in which $R_{13}$ is chosen from H, phenyl, benzyl, and a saturated hydrocarbon radical, preferably an alkyl radical containing 1 to 20 carbon atoms, and $A^-$ is a halide ion. These compounds are described in more detail in U.S. Pat. No. 4,563,347, the disclosure of which is hereby incorporated by reference.

A polymer of formula (V) which is more particularly preferred is known in the CTFA dictionary under the name "Trimethylsilylamodimethicone", of formula (VI):

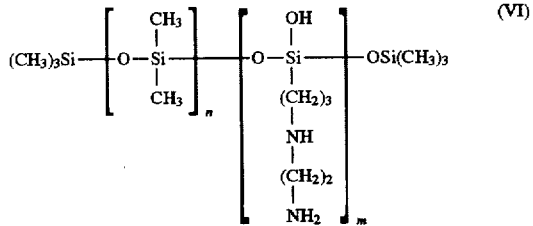

in which n and m are as defined above. A product comprising this type of polymer, more particularly preferred, is that sold by Dow Corning under the name "Dow Corning Q2 7224".

Other cationic silicones which can also be used in the composition according to the present invention are polymers of formula (VII):

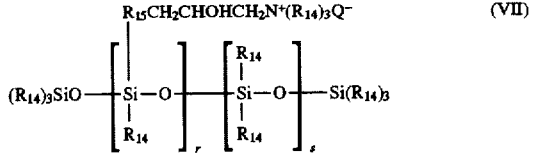

in which $R_{14}$ is a hydrocarbon radical containing 1 to 18 carbon atoms, especially an alkyl or alkenyl radical, and preferably methyl, $R_{15}$ is a hydrocarbon radical, preferably an alkylene radical containing 1 to 18 carbon atoms or an alkyleneoxy radical containing 1 to 18 carbon atoms, and preferably 1 to 8 carbon atoms, $Q^-$ is a halide ion, and preferably a chloride ion, r is a mean statistical value ranging from 2 to 20, preferably from 2 to 8, and s is a mean statistical value ranging from 20 to 200, preferably from 20 to 50. These compounds are described in more detail in U.S. Pat. No. 4,185,087, the disclosure of which is hereby incorporated by reference.

A polymer of this type which is more particularly preferred is that sold by Union Carbide under the name "Ucar Silicone Ale 56".

In the conditioning and detergent composition according to the present invention, the conditioner system generally represents (in concentrations by weight relative to the overall composition): (I) $C_{14}$–$C_{22}$ fatty alcohol(s): from approximately 1 to 10%, preferably from approximately 1 to 8%; (ii) cationic surfactant(s) of the quaternary ammonium salt type: from approximately 0.3 to 10%, preferably from approximately 0.5 to 8%; and (iii) cationic silicone(s): from 0 to approximately 10%.

B—WASHING BASE

The at least one nonionic surfactant of the alkylpolyglycoside type which is used within the scope of the present invention comprises products which are well known per se, and may be represented more particularly by the following general formula (VIII):

$$R_{16}\text{—}O\text{—}(R_{17}O)_t\text{—}(G)_v \quad \text{(VIII)}$$

in which $R_{16}$ is selected from linear or branched alkyl and alkenyl radicals containing 8 to 24 carbon atoms, and alkylphenyl radicals whose linear or branched alkyl radical contains approximately 8 to 24 carbon atoms, $R_{17}$ is an alkylene radical containing 2 to 4 carbon atoms, G is a reduced sugar containing 5 to 6 carbon atoms, t is a value ranging from 0 to 10 and v is a value ranging from 1 to 15.

Preferred alkylpolyglycosides according to the present invention are compounds of formula (VIII) in which $R_{16}$ is, more particularly, selected from linear or branched alkyl and alkenyl radicals containing 9 to 14 carbon atoms, t is a value ranging from 0 to 3, and more particularly still is 0, G is glucose, fructose or galactose. The degree of polymerization (S) of the saccharide, i.e. the value of v in the formula (VIII), can range from 1 to 15. According to the invention, preference is given to reduced sugars containing 80%, or more, of sugars whose degree of polymerization (S) has a value ranging from 1 to 4.

Compounds of formula (VIII) are represented in particular by the products sold by HENKEL under the name APG, such as the products APG 300, APG 350, APG 500, APG 550, APG 625, APG base 10–12; the products sold by SEPPIC under the names TRITON CG 110 (or ORAMIX CG 110) and TRITON CG 312 (or ORAMIX NS 10); and those sold by BASF under the name LUTENSOL GD 70.

It is also possible, according to the invention, to combine, with the nonionic surfactant of the alkylpolyglycoside type, a surfactant of amphoteric or zwitterionic type.

The amphoteric or zwitterionic surfactants, the nature of which is not critical within the context of the present invention, can in particular be (non-limiting list):

aliphatic tertiary or secondary amine derivatives in which the aliphatic radical is a linear or branched chain containing 8 to 18 carbon atoms and containing at least one water-solubilizing anionic group (for example carboxylate, sulphonate, sulphate, phosphate or phosphonate), ($C_8$–$C_{20}$ alkyl)betaines, sulphobetaines, ($C_8$–$C_{20}$ alkyl) amido($C_1$–$C_6$ alkyl)betaines or ($C_8$–$C_{20}$ alkyl) amido ($C_1$–$C_6$ alkyl)sulphobetaines.

Among the amine derivatives, mention may be made of the products sold under the name MIRANOL, as are described in U.S. Pat. Nos. 2,528,378 and 2,781,354, the disclosures of which are hereby incorporated by reference, and classified in the CTFA dictionary, 3rd edition, 1982, under the names Amphocarboxyglycinates and Amphocarboxypropionates.

In accordance with the present invention, more particular preference is given to the use of amphoteric surfactants belonging to the group of the betaines.

In the conditioning and detergent composition according to the present invention, the washing base generally represents (in concentrations by weight relative to the overall composition): (i) nonionic surfactant(s) of the alkylpolyglycoside type: from approximately 5 to 30%, preferably from approximately 8 to 25%; and (ii) amphoteric or zwitterionic surfactant(s): from 0 to approximately 10%.

C—STABILIZER SYSTEM

According to an essential characteristic of the present invention, the stabilizer system comprises a glycol mono- or distearate (commercial stearates contain 70% by weight of $C_{18}$ chains and 30% by weight of $C_{16}$ chains) in combination with a crosslinked polymer of methacryloyloxyethyltrimethylammonium chloride. Polymers of this kind are sold, in particular, by ALLIED COLLOIDS, in 50% solution in mineral oil, under the trade names SALCARE SC92 (crosslinked copolymer of methacryloyloxyethyltrimethylammonium chloride and acrylamide) and SALCARE SC95 (crosslinked homopolymer of methacryloyloxyethyltrimethylammonium chloride).

A polymer which is more particularly preferred according to the present invention is the 42/58 copolymer of methacryloyloxyethyltrimethylammonium chloride and acrylamide (% expressed by weight).

In the conditioning and detergent composition according to the present invention, the stabilizer system generally represents (in concentrations by weight relative to the overall composition): (I) glycol mono- or distearate: from approximately 0.1 to 6%, and preferably from approximately 0.2 to 4%; and (ii) crosslinked polymer of methacryloyloxyethyltrimethylammonium chloride: from approximately 0.2 to 3%, and preferably from approximately 0.4 to 2%.

The conditioning and detergent composition according to the present invention may also contain, in addition to the three abovementioned systems (A), (B) and (C) which characterize it, other ingredients or active agents which are well known in the field of shampoos or conditioners, provided of course that their introduction into the composition impairs neither its stability nor the properties to which the present invention relates. Among these compounds mention may be made, by way of example, of polyethoxylated fatty alcohols, fatty esters, vitamins, solvents, sequestering agents, thickeners, softeners, foam modifiers, pearlescence agents, moisturizers, anti-dandruff or antiseborrhoeic agents, sunscreens, dyes, perfumes, preservatives, etc.

The composition according to the invention can be in the form of a more or less liquid, preferably a thick liquid, or a cream or gel.

Specific but by no means limiting examples illustrating the invention will now be given.

EXAMPLE 1

A conditioning and detergent composition according to the invention was prepared, having the following composition (a.i. indicates active ingredient):

Alkyl(C9/C11)polyglycoside (1.4) in 40%
aqueous solution . . . 14 g a.i.

Cocoylamidopropyld imethylhydroxypropylsulphobe-
taine
in 50% aqueous solution . . . 2.5 g a.i.

50/50 cetyl stearyl (C16/C18) alcohol
(% by weight) . . . 5 g

42/58 copolymer of methacryloyloxyethyltrimethy-
lammonium
chloride and acrylamide
(% expressed by weight), sold by ALLIED
COLLOIDS as a 50% dispersion in mineral
oil under the name SALCARE SC 92 . . . 0.5 g a.i.

Glycol distearate (C16/C18) 30/70 (%
by weight) . . . 2 g a.i.

Behenyltrimethylammonium chloride, 80%
by weight in a 15/85 water/isopropanol
mixture (% expressed by weight) . . . 2.4 g a.i.

Cationic silicone: "DC 939 cationic
emulsion" from Dow Corning . . . 0.88 g a.i.

Preservatives, fragrances . . . qs

Demineralized water . . . qs for 100 g

This composition was found to be stable for two months at a temperature of 45° C.

Hair was washed using this composition. It was found that the hair was very soft during this application.

It was subsequently rinsed under running water. Before drying, it was observed that it was also very soft in the wetted state and was easy to disentangle.

COMPARATIVE EXAMPLES 2 and 3

The composition of Example 1 was reproduced but without introducing glycol distearate. The resulting composition (Example 2) became unstable after only 3 days at a temperature of 45° C.

The composition of Example 1 was reproduced but without introducing the 42/58 copolymer of methacryloyloxy-ethyltrimethylammonium chloride and acrylamide (SALCARE SC 92). The resulting composition (Example 3) became unstable in 13 days at a temperature of 45° C.

What is claimed is:

1. A conditioning and detergent composition for use on hair, said composition comprising, in an aqueous medium:
   (A) a conditioner system comprising (i) at least one $C_{14}-C_{22}$ fatty alcohol and (ii) at least one cationic surfactant selected from quaternary ammonium salts,
   (B) a washing base comprising (i) at least one alkylpolyglycoside nonionic surfactant, and
   (C) a stabilizer system comprising (i) at least one stearate, wherein said at least one stearate is a glycol monostearate or a glycol distearate and (ii) at least one cross-linked polymer of methacryloyloxyethyl-trimethylammonium chloride.

2. A composition according to claim 1, wherein said conditioner system (A) further comprises at least one cationic silicone.

3. A composition according to claim 1, wherein said washing base (B) further comprises at least one surfactant, wherein said at least one surfactant is an amphoteric or a zwitterionic surfactant.

4. A composition according to claim 1, wherein said at least one $C_{14}-C_{22}$ fatty alcohol is cetyl alcohol, stearyl alcohol, or cetyl stearyl alcohol.

5. A composition according to claim 1, wherein said at least one quaternary ammonium salt cationic surfactant is a quaternary ammonium salt of formula (I):

in which $R_1$ to $R_4$, which can be identical or different, are an aliphatic radical containing 1 to 22 carbon atoms, or an aromatic, alkoxy, polyoxyalkylene, alkylamide, hydroxyalkyl, aryl or alkylaryl radical containing 12 to 22 carbon atoms; and $X^-$ is an anion selected from halides, phosphates, acetates, lactates and alkyl sulphates, an imidazolinium quaternary ammonium salt of formula (II):

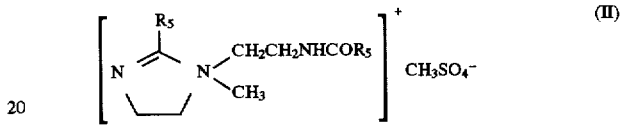

in which $R_5$ is a mixture of alkenyl and/or alkyl radicals containing 13 to 21 carbon atoms and derivatives of tallow fatty acids, or a quaternary diammonium salt of formula (III):

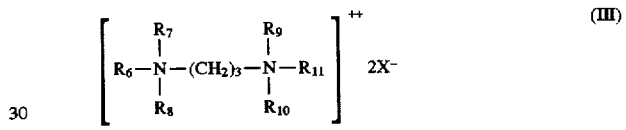

in which $R_6$ is an aliphatic radical containing 16 to 22 carbon atoms, $R_7$, $R_8$, $R_9$, $R_{10}$ and $R_{11}$ are independently selected from hydrogen and an alkyl radical containing 1 to 4 carbon atoms, and $X^-$ is an anion selected from halides, acetates, phosphates and sulphates.

6. A composition according to claim 5, wherein said quaternary ammonium salts of formula (I) include dialky-ldimethylammonium chloride and alkyltrimethylammonium chloride in which the alkyl radical contains 12 to 22 carbon atoms.

7. A composition according to claim 6, wherein said dialkyldimethylammonium chloride is distearyldimethylammonium chloride and said alkyltrimethylammonium chloride is cetyltrimethylammonium chloride or behenyltrimethylammonium chloride.

8. A composition according to claim 5, wherein said quaternary ammonium salt of formula (I) is stearamidopropyldimethyl(myristyl acetate)ammonium chloride.

9. A composition according to claim 7, wherein said alkyltrimethylammonium chloride is behenyltrimethylammonium chloride.

10. A composition according to claim 1, wherein said at least one cationic silicone is an amodimethicone of formula (IV):

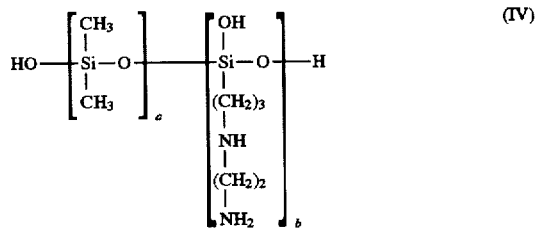

in which a and b are integers depending on the molecular weight, the number average molecular weight being from 5000 to 10,000.

11. A composition according to claim 10, wherein said amodimethicone is combined with hexadecyltrimethylammonium chloride and with polyethoxylated tridecyl alcohol, wherein said hexadecyltrimethylammonium chloride and said polyethoxylated tridecyl alcohol are emulsifying agents for said amodimethicone.

12. A composition according to claim 1, wherein said at least one nonionic surfactant of the alkylpolyglycoside type is a compound of formula (VII):

$$R_{16}-O-(R_{17}O)_t-(G)_v \qquad (VII)$$

in which $R_{16}$ is selected from linear or branched alkyl and alkenyl radicals containing 8 to 24 carbon atoms, and alkylphenyl radicals whose linear or branched alkyl radical contains 8 to 24 carbon atoms, $R_{17}$ is an alkylene radical containing 2 to 4 carbon atoms, G is a reduced sugar containing 5 to 6 carbon atoms, t is a value ranging from 0 to 10 and v is a value ranging from 1 to 15.

13. A composition according to claim 12, wherein $R_{16}$ is selected from linear or branched alkyl and alkenyl radicals containing 9 to 14 carbon atoms, t is 0, G is glucose and v has a value from 1 to 4.

14. A composition according to claim 3, wherein said at least one surfactant selected from amphoteric and zwitterionic surfactants is a betaine.

15. A composition according to claim 14, wherein said betaine is a ($C_8$–$C_{20}$ alkyl)betaine, a sulphobetaine, a ($C_8$–$C_{20}$ alkyl)amido($C_1$–$C_6$ alkyl)betaine or a ($C_8$–$C_{20}$ alkyl) amido($C_1$–$C_6$ alkyl)sulphobetaine.

16. A composition according to claim 1, wherein said at least one crosslinked polymer of methacryloyloxyethyltrimethylammonium chloride is a crosslinked copolymer of methacryloyloxyethyltrimethylammonium chloride and acrylamide.

17. A composition according to claim 1, wherein said at least one $C_{14}$–$C_{22}$ fatty alcohol is present in concentrations by weight of from 1 to 10% relative to the total weight of the composition.

18. A composition according to claim 1, wherein said at least one cationic surfactant is present in concentrations by weight of from 0.3 to 10% relative to the total weight of the composition.

19. A composition according to claim 2, wherein said at least one cationic silicone is present in concentrations by weight up to 10% relative to the total weight of the composition.

20. A composition according to claim 1, wherein said at least one alkylpolyglycoside nonionic surfactant is present in concentrations by weight of from 5 to 30% relative to the total weight of the composition.

21. A composition according to claim 3, wherein said at least one surfactant selected from amphoteric and zwitterionic surfactants is present in concentrations by weight up to 10% relative to the total weight of the composition.

22. A composition according to claim 1, wherein said at least one stearate selected from glycol monostearate and glycol distearate is present in concentrations by weight of from 0.1 to 6% relative to the total weight of the composition.

23. A composition according to claim 1, wherein said at least one crosslinked polymer of methacryloyloxyethyltrimethylammonium chloride is present in concentrations by weight of from 0.2 to 3% relative to the total weight of the composition.

24. A composition according to claim 1, wherein said composition is in the form of a liquid, a cream or a gel.

25. A method for the simultaneous care and cleaning of the hair, said method comprising the step of applying to the hair a composition as defined in claim 1 in an amount effective to both condition and clean said hair.

* * * * *